(12) United States Patent
Lauer (10) Patent No.: US 11,697,013 B2
(45) Date of Patent: Jul. 11, 2023

(54) MEDICAL FLUID COUPLING AND A LATCHING CONNECTOR FOR ESTABLISHING A FLUID COMMUNICATION BETWEEN TWO SYSTEMS

(71) Applicant: Fresenius Medical Care Deutschland GmbH, Bad Homburg (DE)

(72) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 130 days.

(21) Appl. No.: 17/005,887

(22) Filed: Aug. 28, 2020

(65) Prior Publication Data

US 2020/0391020 A1   Dec. 17, 2020

Related U.S. Application Data

(63) Continuation of application No. 15/554,361, filed as application No. PCT/EP2016/054306 on Mar. 1, 2016, now Pat. No. 10,786,663.

(30) Foreign Application Priority Data

Mar. 2, 2015   (DE) .................... 10 2015 102 990.1

(51) Int. Cl.
  *A61M 39/10*   (2006.01)
  *A61M 39/22*   (2006.01)
  *A61M 39/00*   (2006.01)
(52) U.S. Cl.
  CPC .  *A61M 39/1011* (2013.01); *A61M 2039/0036* (2013.01); *A61M 2039/1027* (2013.01);
(Continued)

(58) Field of Classification Search
  CPC ...... A61M 39/1011; A61M 2039/1027; A61M 2039/229; A61M 2039/0036;
(Continued)

(56) References Cited

U.S. PATENT DOCUMENTS 4,770,445 A  9/1988 Steer et al.
4,787,429 A  11/1988 Valentini et al.
(Continued)

FOREIGN PATENT DOCUMENTS

CN  87105316  7/1988
DE  102011108787 A1  1/2013
(Continued)

OTHER PUBLICATIONS

PCT International Search Report for PCT/EP2016/054306, dated Aug. 23, 2016, 5 pages.
(Continued)

*Primary Examiner* — Zachary T Dragicevich
(74) *Attorney, Agent, or Firm* — Fish & Richardson P.C.

(57) ABSTRACT

A medical fluid coupling for connecting a fluid line to a connection section of a blood treatment apparatus or for connecting to a connecting adapter comprises at least one main body. The main body includes a first latching element with a first section. The first section is designed to be elastically bendable and/or elastically tiltable. The main body may optionally include a second latching element with a second section. At least one of the first latching element and the second latching element comprises a recess for receiving a protrusion of the connection section and/or a protrusion to reach into a recess of the blood treatment apparatus or of the connecting adapter.

16 Claims, 7 Drawing Sheets

(52) U.S. Cl.
CPC ............... *A61M 2039/1072* (2013.01); *A61M 2039/229* (2013.01); *A61M 2205/0216* (2013.01)

(58) Field of Classification Search
CPC ... A61M 2039/0216; A61M 2039/1072; F16L 37/133
USPC .......................................................... 604/533
See application file for complete search history.

(56) References Cited

U.S. PATENT DOCUMENTS

| | | | |
|---|---|---|---|
| 5,496,274 | A | 3/1996 | Graves et al. |
| 5,688,254 | A | 11/1997 | Lopez et al. |
| 10,786,663 | B2 | 9/2020 | Lauer |
| 2007/0073270 | A1 | 3/2007 | Christensen et al. |
| 2008/0090445 | A1 | 4/2008 | Luzbetak et al. |
| 2009/0287140 | A1 | 11/2009 | Rittman |
| 2013/0030348 | A1 | 1/2013 | Lauer |
| 2013/0245530 | A1 | 9/2013 | Brandl et al. |
| 2013/0245531 | A1 | 9/2013 | Brandl et al. |
| 2015/0260325 | A1 | 9/2015 | Quick |
| 2015/0297830 | A1 | 10/2015 | Okiyama |
| 2018/0050186 | A1 | 2/2018 | Lauer |
| 2018/0064923 | A1 | 3/2018 | Takeuchi |

FOREIGN PATENT DOCUMENTS

| | | |
|---|---|---|
| DE | 202012101283 | 7/2013 |
| DE | 102012005187 | 9/2013 |
| DE | 102012005189 | 9/2013 |
| EP | 2881138 | 6/2015 |
| GB | 2091365 | 7/1982 |
| JP | 2001-190658 | 7/2001 |
| JP | 2007-307302 A | 11/2007 |
| JP | 2010-506611 | 3/2010 |
| JP | 2010-137043 | 6/2010 |
| JP | 2014-30540 | 2/2014 |
| JP | 2014-525791 A | 10/2014 |
| WO | WO 1990/005559 | 5/1990 |
| WO | WO 2007/118235 | 10/2007 |
| WO | 2014/021271 A1 | 2/2014 |
| WO | WO 2014/021390 | 2/2014 |

OTHER PUBLICATIONS

PCT International Preliminary Report on Patentability in Application No. PCT/EP2016/054306, dated Sep. 5, 2017, 11 pages (English Translation).

MEDICAL FLUID COUPLING AND A LATCHING CONNECTOR FOR ESTABLISHING A FLUID COMMUNICATION BETWEEN TWO SYSTEMS

CROSS-REFERENCE TO RELATED APPLICATIONS

The present application is a continuation application of U.S. application Ser. No. 15/554,361, filed on Aug. 29, 2017, now U.S. Pat. No. 10,786,663, which is the national stage entry of International Patent Application No. PCT/EP2016/054306, filed on Mar. 1, 2016, and claims priority to Application No. DE 10 2015 102 990.1, filed in the Federal Republic of Germany on Mar. 2, 2015. The disclosures of the prior applications are expressly incorporated herein in entirety by reference thereto.

TECHNICAL FIELD

This disclosure relates to a fluid coupling and/or latching connector. It relates further to a system, a blood treatment apparatus or a connecting adapter, a tube line, and a blood treatment machine

BACKGROUND

Connectors for establishing or providing a fluid communication between two systems, which carry or conduct fluid respectively, are known in the prior art.

SUMMARY

Multiple embodiments of fluid couplings or latching connectors for fluid coupling which are designed to be pushed onto or plugged into a connection section are described in this disclosure. The connection section may be part of a blood treatment apparatus, a connecting adapter, a fluid line, or the like. The fluid coupling may be part of a fluid line or fluid communication, for example between the blood treatment apparatus and the fluid line or between the connecting adapter and the fluid line.

The fluid coupling preferably serves a connection of lines, in which medical fluids such as blood or dialysate are carried. Therefore, it may be denoted as a medical fluid coupling.

The fluid coupling may for example serve the connection of a blood treatment apparatus to a fluid line. The former may be a blood filter or a dialyzer. The latter may be a blood or dialysate line.

The connection section may be in particular a tube connector.

The fluid coupling comprises at least one first component which is referred to herein as main body (these two expressions are exchangeable herein), however in certain embodiments it may also be referred to as handle part or housing part. The main body comprises a receiving section for receiving one end of a fluid conduit or pipe of the connection section. The main body further comprises at least one first latching element and one optional second latching element.

The first latching element comprises a first section which is designed to be elastically bendable or tiltable. The first section is only preferably arranged at a free end of the first latching element or it forms the end of the first latching element at its free end.

The second latching element comprises a section, referred to herein as second section. The latter is purely preferably arranged at one end of the second latching element or it forms the end of the second latching element at its free end. The second latching element is purely optional and it is not indispensable.

At least the first latching element and/or the second latching element comprise a recess or a protrusion. The recess, if any, serves the reception of a protrusion of the connection section, which in turn is part of, e.g., a blood treatment apparatus or of a connecting adapter. The protrusion, if any, serves the engagement or interlocking in a recess of the connection section.

In this, the recess or the protrusion is arranged, when being part of the first latching element, such that it faces the second latching element (and/or the receiving section), and/or vice versa. Additionally or alternatively, the recess or the protrusion is arranged at an inner side of the respective latching elements.

The system described herein includes at least one fluid coupling and at least one connection section, or it comprises both. The fluid coupling and connection section are embodied and provided to latch to each other in a latching connection and preferably in fluid communication. The latter takes place preferably as a non-positive and/or positive connection.

Certain aspects of this disclosure further relate to a blood treatment apparatus or to a connecting adapter with at least one connection section respectively. The connection section is embodied and provided to be latched in a latching connection and preferably in fluid communication with at least one fluid coupling. The connection section may thereby be embodied and provided to have protrusions or recesses which are suitable, designed and/or provided for establishing a latching connection with a fluid coupling while achieving a fluid communication between a fluid conduit of the connection section and the fluid guiding section of the fluid coupling.

The medical or medical technical blood treatment apparatus described herein (hereinafter in short: treatment apparatus) is designed to serve, in connection to a blood treatment machine, for the dialysis, hemodialysis, hemodiafiltration, filtration or apheresis. It may be a blood filter, dialyzer or the like.

The tube line for medical use described herein comprises at least one fluid coupling.

The medical or medical technical blood treatment machine described herein is connected to a blood treatment apparatus in fluid communication. The blood treatment machine may serve for the dialysis, hemodialysis, hemodiafiltration, filtration or apheresis and may comprise devices necessary thereto, like blood pumps etc.

In all of the embodiments, the use of the expression "may be" or "may have" and so on, is to be understood synonymously with "preferably is" or "preferably has," and so on respectively, and is intended to illustrate an embodiment.

Embodiments may comprise one or several of the aforementioned or following features in any combination.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" always as "at least one". This understanding is also equally encompassed in some embodiments as the interpretation that a numeric word, for example, "one" may alternatively mean "exactly one", wherever this is evidently technically possible for the person skilled in the art. Both are encompassed in certain aspects and apply herein to all used numerical words.

The spatial indications "top" and "bottom" are to be understood herein, in case of doubt by the person skilled in the art, as absolute or relative spatial indications which refer to the alignment of the respective component during its common use.

In certain exemplary embodiments described herein, the recess comes to existence when no external forces are applied on the first and/or the second latching element. Thus, by acting on the first and/or second latching element and its elastic deformation, the recess may therefore be removed or its geometry may be changed such that a retaining or holding back of the protrusion is not fluid coupling ensured anymore. Alternatively, acting on the first and/or second latching element and its elastic deformation may change the geometry of the recess such that a retaining or holding the protrusion in all shifting directions is not ensured. The recess is to be observed again when the active, elastic deformation is completed. This can be implemented for example by a design in which the free end section of the first and/or the second latching element is arranged relative to the remaining latching element or to the main body in a tiltable, foldable or movable manner, or otherwise arranged, in particular against material restoring forces or material resistance.

In certain exemplary embodiments, the main body comprises a fluid guiding section extending through its interior which extends through the main body in its longitudinal direction. The fluid guiding section can be a fluid canal.

In certain exemplary embodiments, the main body is integrally formed, in others it is a multi-part.

In certain exemplary embodiments, the protrusion or the protrusions of the connection section are designed as a latching edge. The latter may be circumferential, i.e. surrounding the whole or only sections of the circumference of the component carrying it, e.g. of the connection section.

In certain exemplary embodiments, at least one of the latching elements is designed as latching wing, clamp wing, arm, component which carries the recess or the extension, or the like.

In some exemplary embodiments, the second section of the second latching element is also designed as elastically bendable or elastically tiltable. In such embodiments the latching is carried out by elastically bending or tilting both latching elements. In others, it is enough to elastically bend or tilt only the first latching element. The second latching element, if available, serves as a counter-bearing in case it does not comprise any elastic section.

In certain exemplary embodiments, the first section of the first latching element and, the second section of the second latching element or the receiving section, are in a non-connected state, arranged having a first distance between each other such that, during the process of connecting or for the purpose of connecting the fluid coupling to the connection section, the first distance becomes or has to become a second distance, even if this is only temporarily the case. The second distance may be larger than the first distance.

In certain exemplary embodiments, the first and second distance are situated in the same plane.

In some particular embodiments, the first section of the first latching element and the second section of the second latching element are in one plane or are movable within a common plane for connecting or releasing the connection. This advantageously allows to easily release the connection using only one hand.

In certain exemplary embodiments, the first section of the first latching element and/or the second section of the second latching element is a tiltable section or is arranged in a tiltable manner at a further section of the respective latching element.

In certain exemplary embodiments, the first and/or the second latching element are produced as integral or a one-piece sections of the main body.

In certain exemplary embodiments, an inner diameter of the fluid guiding section of the main body, which particularly extends in longitudinal direction of the main body, remains constant and is between 4.0 and 4.5 mm, and more preferably 4.2 mm.

In certain exemplary embodiments, the main body is made of or comprises a first material. In addition, the fluid coupling comprises a sealing element made of a second material which is different from the first material.

In certain exemplary embodiments, the sealing element comprises a through opening with exactly or at least one inner diameter, which corresponds or is identical to an inner diameter of the fluid guiding section of the main body.

In certain exemplary embodiments, the main body comprises, in addition to the first end area and to the second end area of the fluid guiding section, at least one further opening. The opening is closable by means of a septum and comprises such a septum optionally. This opening is situated in or opens out into, preferably between the first end area and the second end area, the fluid guiding section.

In certain exemplary embodiments, the main body comprises the fluid guiding section as a main canal with a lumen for guiding a first fluid through the fluid coupling. The main body comprises further a secondary canal outlet of a secondary canal for adding a second fluid into the main canal. In this, the fluid coupling comprises at least one actuating element which is arranged relative to the main body to be transferrable, positionally adjustable, or movable between a first position and a second position. Furthermore, the fluid coupling comprises a sealing section which is arranged, to be twistable when the actuating element is being transferred from one position into the other, between a first position of the sealing section, in which the sealing section does not close or cover the secondary canal outlet (open position), and a second position of the sealing section, in which the sealing section closes or covers the secondary canal outlet (closed position).

In certain exemplary embodiments of the system, the inner diameter of the fluid guiding section and an inner diameter of a fluid conduit of the connection section are substantially or completely the same in an area of a front face assigned to or facing the fluid guiding section.

In certain exemplary embodiments of the system, the inner diameter of the fluid guiding section, an inner diameter of a sealing element and an inner diameter of the fluid conduit are substantially or completely the same in an area of a front face assigned to or facing the fluid guiding section.

In certain exemplary embodiments, the tube line is maximally 200 mm (millimeter), or 150 mm maximally, or maximally 100 mm long.

In some exemplary embodiments, the fluid coupling is not a screw connector, the fluid coupling comprises no thread and/or no thread is provided, for its connection, with any threaded nut or cap nut, nor is it connectable thereto.

In some particular embodiments, the fluid coupling is part of the fluid line, i.e. that a section of the fluid coupling, herein denoted as fluid guiding section, is perfused or may be perfused by fluid when used as intended, as this section is part of a flow path or conduit.

The tube which is connected to the fluid coupling in some embodiments may itself be connected to a blood cassette. The blood cassette may be a hard part, which is closed, at least at one side, against the environment by a film and/or is connected to the film.

In certain embodiments, the first latching element and/or the second latching element are designed as a bending fork. The first latching element and/or the second latching element may comprise one or several detent lugs which may be provided at the bending fork.

In exemplary embodiments, the recesses of at least one latching element are designed at an inner side or a lower side thereof.

In some embodiments, the fluid coupling is designed to be connected to the connection section exclusively by latching the first latching element and/or the second latching element, and by inserting the fluid conduit or a face section thereof in the receiving section as well as optionally by sliding on of an external conduit or pipe of the connection section onto the receiving section.

In some exemplary embodiments, the main canal is a pipe.

In some exemplary embodiments, the sealing section is arranged or designed not to impair an access to the main canal for the first fluid neither in its first position nor in its second position.

In some exemplary embodiments, there is no section of the sealing section in the lumen of the main canal.

In some exemplary embodiments, the main canal comprises in addition to the secondary canal outlet a septum outlet which, during use of the fluid coupling, is closed by a septum penetrable by a cannula.

In some exemplary embodiments, the secondary canal outlet and/or the septum outlet extend or open up into a straight extending section of a cross section of the lumen or its circumference of the main canal.

In some exemplary embodiments, the sealing section comprises a front-face sealing surface which is arranged to be moved during the rotation of the sealing section along a rotation curve from a first position into a second position on the rotation curve, wherein the sealing surface closes or covers, in the second position, the secondary canal outlet, wherein the sealing surface does not close or cover, in the first position, the secondary outlet, and wherein the sealing surface extends parallel to a main cross section plane and/or vertically to a rotation axis of the sealing section.

In some exemplary embodiments, the sealing section comprises a sealing lug, which protrudes from it in an axial direction of the sealing section, wherein the sealing lug is arranged to be moved on a rotation curve from a first position into a second position on a rotation curve, at a rotation of the actuating element or at the transferring of the actuating element from one position into another, wherein the sealing lug does not close or cover the secondary canal outlet in the first position, and wherein the sealing lug closes or covers the secondary canal outlet in the second position.

In some exemplary embodiments the housing element comprises at least one section which comprises a recess for receiving the sealing lug movable herein, and which comprises or abuts or is adjacent to the secondary canal outlet.

In some exemplary embodiments, the sealing lug comprises a groove which is open towards both a front face of the sealing lug and to a lateral side surface or peripheral surface of the sealing section.

In some exemplary embodiments, the groove is disposed, in the first position of the sealing section, against an opening of a secondary canal pipe such that it continues the fluid path of the secondary canal pipe across the sealing section, wherein the groove is not, in the second position of sealing section, in fluid communication with the secondary canal pipe or its opening.

In some exemplary embodiments, the sealing section comprises in addition to its front-face sealing surface or in addition to its sealing lug, a projecting, closed sealing structure which, in the second position of the sealing section, closes the opening of the secondary canal pipe or prevents an exit or escape of fluid out of the opening.

In some exemplary embodiments, the sealing section is a separate sealing element.

In some exemplary embodiments, the sealing section comprises at least one pierceable septum.

In some exemplary embodiments, both the septum outlet and the secondary canal opening are arranged together in one half of a cross section of the main canal.

In some exemplary embodiments, the fluid coupling comprises a receiving section for receiving or fixing, in particular temporarily, a protection cap, in particular provided for covering a secondary canal pipe or a secondary canal connector, onto the fluid coupling.

The fluid coupling comprises preferably a fluid guiding section through which fluid may flow through the fluid coupling in a longitudinal direction thereof. The fluid guiding section defines therewith the longitudinal direction or longitudinal axis of the fluid coupling.

The fluid guiding section comprises a first end area and, opposite to the latter, a second end area. Both the first end area and the second end area may connect the fluid guiding section to the exterior of the main body.

The fluid guiding section may optionally have the smallest diameter of all structures of the main body perfused during use by fluid in the longitudinal direction of the main body.

In some exemplary embodiments, the perfused diameter or inner diameter of the fluid guiding section is smaller than the inner diameter of the first connection section.

In some exemplary embodiments, the perfused diameter or inner diameter of the fluid guiding section may be smaller than the inner diameter of the tubular expansion of the second connection section.

Both the first latching element and the second latching element may have a width—e.g. indicated as length or circumference degree, which is each only a fraction of the circumference of the fluid coupling.

For establishing a fluid communication between the fluid guiding section and the fluid conduit of the connection section, the fluid coupling comprises in some embodiments a free space between the outer circumference of the tubular expansion of the second connecting section and the latching elements. This free space is optional and provided to receive an outer conduit or pipe of the connection section herein.

The tubular expansion may be designed to receive within its interior both the sealing element and at least also sections of the fluid conduit of the connection section.

The sealing element comprises in some particular embodiments an opening which optionally comprises at least two opening cross sections or inner diameters different from each other. The sealing element may optionally comprise in addition at least two outer diameters different from each other.

In addition, the sealing element may comprise a peripheral bead at its end which is, during use, adjacent to the second end area. The peripheral bead may, when it is inserted in an optional peripheral groove at the inner circumference of the second connecting section, account for a further improvement of the sealing effect.

The fluid coupling may be exactly two-part, and may comprise, in addition to the main body itself, a sealing element.

The tubular expansion has in some exemplary embodiments more than only one diameter, each of which is larger than the inner diameter of the second end area or of the fluid guiding section.

Some or all of the embodiments may encompass one or several of the aforementioned or following advantages.

The fluid coupling described herein may offer advantages in that the fluid coupling comprises or requires no threads and/or no union nut which in turn advantageously allows a manual arrangement of the fluid coupling relative to a blood treatment apparatus which comprises the connection section. In contrast to, for example the tightening of the union nut, the fluid coupling remains in the desired rotation position. The unwanted rotation of the connector observed in the case of union nuts due to a competing friction situation, in the last almost 30 degrees of tightening, between the union nut and the connector and the connector and the blood treatment apparatus does not occur. Thereby, the desired or intended position or rotating orientation with which the fluid coupling is plugged onto the connection section, is advantageously maintained. Further functions may therefore be well or suitably integrated, for example a pierceable septum in the connector. The pierceable septum often necessitates an exact rotational orientation with respect to the dialyzer and with respect to the blood treatment device. This is beneficial as it may lessen the space taken up by apparatuses, tubes, and equipment during treatment.

Furthermore, the fluid coupling spares the user a troublesome or difficult unscrewing during which, undesirably high and potentially damaging torques may be applied.

A passive contact protection of the relevant areas of the connecting or connection outlet is advantageously achieved. Therefore no protection cap is required and contamination through a failure in the common handling is advantageously prevented.

Advantageously, the fluid coupling does not need to have a material which comprises a plasticizer. Materials containing plasticizer are known in connectors of the prior art; they serve a better sealing when screwing on the connector with an ergonomically acceptable torque. They are not required due to a lack of a screw connection.

The fluid coupling may advantageously be used for connecting arbitrarily short tubes, as no twisting is applied which may lead to tube buckling.

The fluid coupling is optimized with respect to its handling. It is advantageously easily connected and released, which may take place using one hand and without requiring a large space for the hand or hands. This is different compared to the operation of thread connectors known in the art.

The fluid coupling is connected only by means of plugging or latching. The completion of the connecting process is clearly transmitted to the user, for example through the audible and/or tactile click at the fluid coupling, namely when the latching elements glide over the protrusions of the connection section and the protrusions latch into the recesses or latching elements (or protrusions of the latching elements into the recesses of the connection section). Hereby, the user receives reliable feedback regarding whether the desired connection has been achieved or not.

If a malfunction occurs, the fluid coupling may be manually removed by fluid coupling manually spreading apart the latching element (which may comprise e.g. snap tongues or tiltable sections as elastic, first and second sections) or by pressing the latching elements together, depending on the embodiment. A removal by the user is however not possible. The latching is furthermore optically directly verifiable.

The fluid coupling comprises, in its interior, no dead zones of the flow, dead spaces or sharp edges. This contributes to a good ventilation, rinsing or flushing, and hemocompatibility. The same also applies to the junction between the fluid guiding section and fluid conduit of the connection section.

In exemplary embodiments, the diameter of the fluid guiding section, which may also be denoted as canal diameter, is constant; in some embodiments, it is comparatively small (e.g. between 3.5 and 5.0 mm, preferably 4.0 to 4.5 mm, particularly preferred is 4.2 mm, preferably smaller than 6.0 mm). Both reduce the probability of the remaining fluid exiting when disconnecting the fluid coupling.

In exemplary embodiments, the sealing element, e.g. the sealing ring, is made of silicon rubber. Such material selection contributes to the fact that the fluid coupling is well automatically mountable and easily steam-sterilizable. This material selection contributes also to a tolerance-insensitive radial sealing due to the very distinct axial flexibility of the sealing element and to a bridging of dimensional tolerance with no dead spaces.

The presence or use of silicon rubber in the material in this, is only about one third of that required, for example, in known check valves. The fluid coupling is distinguished through an inexpensive production price.

In exemplary embodiments, the second end area of the fluid guiding section, which is connected during use in fluid communication to either the sealing element or, when no sealing element is provided, to a front face of the fluid conduit of the connection section, is shifted back as against the tubular expansion. The latter ensures a permanent contact protection of the surfaces of the fluid coupling relevant during the connection. A protection cap for the fluid guiding section may advantageously be dispended with. Such a solution also offers protection against cough drips.

In exemplary embodiments, the main body and, if any, the septum hood is made of PP (Polypropylen).

The septum may be made of known septum rubber.

In some particular exemplary embodiments, the septum is advantageously flush without an inner diameter step with the fluid guiding section, which is exemplarily designed as a blood canal.

In some exemplary embodiments, the access to the septum by the user advantageously remains in a constant rotating position with respect to the connection section. Advantageously, the septum access does not jointly rotate when using the fluid coupling.

In some exemplary embodiments, the cover is connected through a film-snap-joint to the main body of the fluid coupling. This allows a distinct protection against coughing over the septum. In addition, the period of safe sterility is extended or prolonged. However, also already due to the shifted-back position of the septum with regard to the surface of the main body, the septum may advantageously be considered to be permanently contact-protected and yet may be easily sprayed with disinfectant.

In some exemplary embodiments, the septum hood is produced in a simple and cost-effective manner by means of on-off tools. It allows, nevertheless, a non-releasable and a mechanically precise or accurate latching with the fluid coupling.

In some embodiments, the septum hood comprises at least one element by means of which a pressing of the septum is carried out, preferably continuously. Such pressing protects the septum from accidently being or becoming released or leaky, particularly due to a prevailing fluid pressure in the fluid guiding section adjacent to the septum.

Some exemplary embodiments are advantageously compatible with steam sterilizing methods, which are advantageous as breakthroughs or apertures and/or drainage structures of some embodiments may be difficult to sterilize using other methods.

In some embodiments, the fluid coupling is connectable through plugging and latching, without necessitating a rotating movement, for example a thread connection. Accordingly, an insertion in an improper orientation with a subsequently required rotation of the tube may advantageously be prevented. In addition, there is no twisting accompanied by or with generation of a restoring force. With that, an unwanted release of the connection may be prevented. Thereby, very short tubes (100 mm long or shorter) may be used, for their connection when no rotating movement is required. There is no twisting (kinking) even in connecting very short tubes. Short tubes are cost effective as less tube material is used. Furthermore, less blood is extra corporally conducted than in the known, long tubes. Additionally, long tubes are hard to handle as they may for example get jammed when closing doors, lids etc. of the treatment apparatus, for instance when pressing the blood cassette behind a door of the treatment apparatus. These two last-mentioned disadvantages may be reduced or cancelled in some embodiments.

In some exemplary embodiment, additional tube connections for luer addition tubes or with direct luer-connecting pieces or nozzles are optionally simply integrated or integratable in the main body of the fluid coupling for luer addition tubes or with direct luer-connecting pieces or nozzles.

In some exemplary embodiments, the latching elements are arranged symmetrically, preferably in mirror symmetry. Such symmetry advantageously allows to actuate the latching elements easily and without tension, for release of the connection using one hand.

The fluid coupling and the integrated septum are beneficial, in comparison with the known chain-arrangement of a known septum-tube addition site and with a known screw connector in a connecting tube.

An advantage of certain aspects may be to propose a further connector for providing a fluid communication between two systems which carry a medical fluid. Furthermore, suitable devices, which are directly or indirectly connected to the connector, are to be specified.

Some embodiments shall be exemplarily explained with regard to the accompanying drawings in which identical reference numerals refer to the same or similar elements. The following applies in the partly highly simplified figures:

DETAILED DESCRIPTION OF ILLUSTRATIVE EMBODIMENTS

Figure 1:
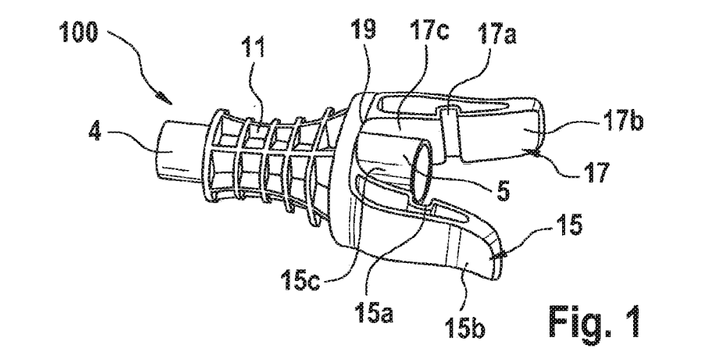
FIG. 1 shows a perspective view of a main body of a fluid coupling in a first embodiment.

FIG. 1 shows a perspective view of the main body of an exemplary fluid coupling 100 in a first embodiment. Fluid coupling 100 is hereinafter described also with reference to FIG. 2 and FIG. 3.

The fluid coupling 100 comprises or defines a fluid guiding section 1, through which fluid may flow through the fluid coupling 100 in a longitudinal direction thereof. The fluid guiding section 1, thus, defines or determines the longitudinal direction or longitudinal axis of the fluid coupling 100.

The fluid guiding section 1 comprises one first end area 2 and, opposite to it, one second end area 3. Both the first end area 2 and the second end area 3 can connect the fluid guiding section 1 to the exterior of the main body, as shown in FIG. 1.

The fluid guiding section 1 may be designed as a canal, channel, conduit, or lumen. It may optionally comprise the smallest diameter of all structures of the main body through which fluid flows during use in the longitudinal direction of the main body.

The fluid coupling 100 comprises a first connecting section 4 in the area of the first end area 2 and a second connecting section 5 in the area of the second end area 3. The second connecting section 5 is exemplarily designed as tubular expansion which is here denoted likewise with the reference numeral 5.

The first connecting section 4 serves as a fluidic connection of the fluid coupling 100, of its first end area 2 or of the fluid guiding section 1 with a fluid system, e.g. to the end of a tube line.

Figure 3:
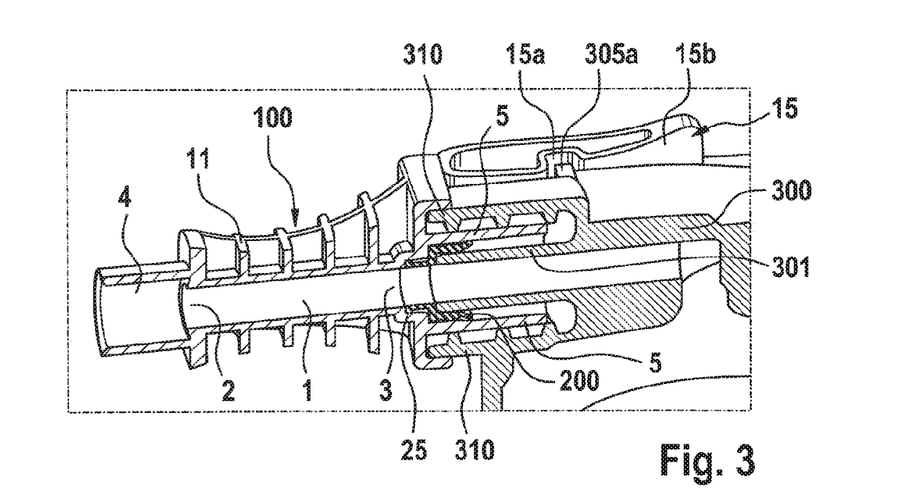
FIG. 3 shows a slightly perspective, longitudinal section view of the fluid coupling of the first embodiment with the main body of FIG. 1 and the sealing element of FIG. 2, wherein the fluid coupling is connected to a connection section.

The second connecting section 5 serves as a fluidic connection of the fluid coupling 100, of its second end area 3 or of the fluid guiding section 1 with a fluid conduit 301 of the connection section 300 shown first in FIG. 3. The fluidic connection between the second end area 3 and the connection section 300 is, in the exemplary embodiment of FIG. 1, indirect, as the second end area 3 is in direct contact to a sealing element 200, but not connected directly to the connection section 300 itself. The sealing element 200 is itself in direct contact to the connection section 300 and is in fluid communication therewith.

The second connecting section 5 serves as receiving section for one end of the fluid conduit 301.

In the exemplary embodiment of FIG. 1, the second connecting section 5, which is herein exemplarily designed as tubular expansion 5, is lined up to the second end area 3 with a larger distance to the first end area 2 than to the second end area 3.

The perfused diameter or inner diameter of the fluid guiding section 1 is, in exemplary embodiments such as the one shown in FIG. 1, smaller than the inner diameter of the first connecting section 4. Thus, one end of a tube 30, first shown in FIG. 11, of the non-shown fluid system may be inserted into the first connecting section 4 by gluing or clamping and hence may be inserted into the main body. Due to such design, it may be connected to the main body such that no jump in diameter is caused at the junction of the tube end and the fluid guiding section 1, thereby preventing turbulences due to rapidly changing flow cross sections and dead spaces.

The perfused diameter or inner diameter of the fluid guiding section 1 is, in exemplary embodiments such as the one shown in FIG. 1, additionally or alternatively to what is stated in the previous paragraph smaller than the inner diameter of the tubular expansion of the second connecting section 5. If, as seen in the exemplary embodiment of FIG. 1, the inner diameter of the tubular expansion is larger than that of the fluid guiding section 1, then the sealing element 200 may be inserted into the tubular expansion and thus into the main body and may be connected therewith through clamping or latching, without causing a jump in diameter at the junction of the sealing element 200 and the fluid guiding section 1. The latter advantageously prevents turbulences due to rapidly changing flow cross sections and prevents dead spaces. Furthermore, this design brings the sealing element 200 in contact with the connection section 300, without changing the perfused diameter in the area of the sealing element 200, thereby increasing the sealing effect.

The fluid coupling 100 comprises a first latching element 15 and a purely optionally provided second latching element 17. In the exemplary embodiment of FIG. 1, both protrude in longitudinal direction of the main body over a free end of the second connecting section 5.

The first latching element 15 is elastically designed in a first section 15b thereof, i.e. the end of the latching element 15 shown in FIG. 1 on the right. Optionally, also the second latching element 17 is elastically designed in a second section 17b thereof, the end of the latching element 17 shown in FIG. 1 on the right. Due to their elasticity, the first and second section 15b, 17b may to a certain extent be moved apart from each other under application of force, to move again towards each other after removal of the force. Optionally, the first section 15b and the second section 17b are the sections of the first or second latching element 15, 17 by means of which the latter protrude over the free end of the second connecting section 5.

Both the first latching element 15 and the second latching element 17 have a width which—e.g. indicated as length or circumference degree—each make up only a fraction of the circumference of the fluid coupling 100 in a third area 19, in which both the first latching element 15 and the optional second latching element 17 are connected to the remaining fluid coupling sections. In other words, both latching elements 15, 17 are offset from each other, there is a space between them in the peripheral direction of the fluid coupling 100.

Both the first latching element 15 and the second latching element 17 have, in the exemplary embodiment of FIG. 1, a recess 15a or 17a, respectively. Both recesses 15a, 17a are provided to receive one or several protrusions 305a of the connection section 300, one of which is first shown in FIG. 3. The connection section 300 is releasably coupled to the fluid coupling 100, and vice versa, by receiving the protrusions 305a in the recesses 15a and 17a—and, where appropriate, by leading a fluid conduit 301 of the connection section 300 in the interior of the second connecting section 5 as a reception section, herein exemplarily designed as tubular expansion 5, as well as by pushing an outer pipe 310 (shown first in FIG. 3) over the tubular expansion.

The connection between the protrusions 305a and the recesses 15a and 17a is non-destructively detachable. The fluid coupling 100 is therefore reusable.

To connect the fluid coupling 100 to the connection section 300 as shown in FIG. 3, the fluid coupling 100 is pushed onto the connection section 300. Thereby, the distance between the first latching element 15 and the second latching element 17 increases due to the expanding effect of the protrusions 305a, further increasing until the recesses 15a and 17a slide over the protrusions 305a and receive them due to the elasticity. When this is accomplished, the procedure of connecting, which recognizably is or encompasses latching, is terminated. The desired connection is achieved.

In order to release the connection, the first latching element 15 and, if provided, the second latching element 17 are spread apart manually, i.e. deformed against their elastic resistance, such that the distance between the first section 15b and the second section 17b is enlarged to the point that their recess 15a or 17a, respectively, sufficiently releases the protrusions 305a, so that it is possible to release the connection section 300 by pulling the fluid coupling 100 or vice versa.

The fluid guiding section 1 may be enveloped by, or may comprise, at its circumference a web-honeycomb structure 11. Due to its inhomogeneous surface texture, one can securely take hold of the fluid coupling 100 by hand. At the same time, it supports the fluid guiding section 1 and protects it from mechanical damage, e.g. by kinking.

The fluid coupling 100 comprises free spaces 15c, 17c, as seen in FIG. 1, between the outer circumference of the tubular expansion of the second connecting section 5 and the latching elements 15, 17, respectively, for establishing a fluid communication between the fluid guiding section 1 and the fluid conduit 301 of the connection section 300. Such free spaces 15c, 17c are optional and provided to receive the sections of the outer conduit or pipe 310 of the connection section 3. The outer pipe 310 encloses the fluid conduit 301 of the connection section 300 located in its interior, for example concentrically.

In some embodiments, the fluid coupling 100 consists of the main body, as it is shown in FIG. 1 or in other embodiments. In other embodiments, the fluid coupling 100 comprises in addition to the main body at least one sealing element 200, as shown in an exemplary embodiment in FIG. 2. The latter exemplary embodiments include the embodiment shown in FIG. 1, in which the sealing element 200 is provided (exemplarily designed as shown in FIG. 2).

The tubular expansion 5 is embodied such that it receives both the sealing element 200 and at least also sections of the fluid conduit 301 of the connection section 300 in its interior as shown in FIG. 3.

Figure 2:
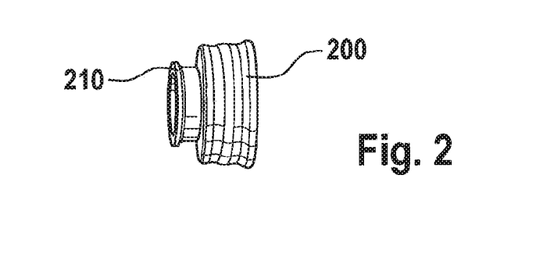
FIG. 2 shows a side view of a sealing element for use with the main body of FIG. 1.

FIG. 2 shows a sealing element 200 optionally designed as a sealing ring and provided to be inserted in the tubular expansion of the second connecting section 5 of the main body of the fluid coupling 100.

The sealing element 200 comprises an opening therethrough having, optionally, at least two different opening cross sections or inner diameters. The sealing element 200 may, optionally, additionally comprise at least two different outer diameters. Both are seen in FIG. 2.

Additionally, the sealing element 200 may comprise at its end, abutting during use the second end area 3, a peripheral bead 210. The peripheral bead 210 may, when it is inserted or guided into an optional peripheral groove 25 at the inner circumference of the second connecting section 5, account for additional improvement of the sealing effect.

FIG. 3 shows the fluid coupling 100 of FIG. 1 with the sealing element 200 of FIG. 2, wherein the fluid coupling 100 is connected in fluid communication with the previously aforementioned connection section 300. Hence, FIG. 3 shows the system in an exemplary embodiment.

It is seen in FIG. 3 how the recess 15a of the first latching element 15 receives the protrusion 305a of the connection section 300. The latching element 15 is illustrated with respect to its inner side, which may be its bottom or lower side.

As seen in FIG. 3, which shows exactly only one latching element, it may be sufficient in some embodiments to ensure the connection between the fluid coupling 100 and the connection section 300 by only exactly one latching element by means of latching, wherein this connection is generated by inserting the fluid conduit 301 into the second connecting section 5 and by snapping or plugging the outer pipe 310 on the outer circumference of the second connecting section 5.

The sealing element 200 comprises a first inner diameter (which is seen at the left end of the sealing element 200 in FIG. 3) which corresponds to the inner diameter of the second end area 3 or the fluid guiding section 1 of the fluid coupling 100. Such correspondence or matching is not necessarily required, however it offers the advantage of a fluidically advantageous passage between the second end area 3 and the sealing element 200 such that turbulences of fluid flowing between sealing element 200 and second end area 3 are prevented or decreased.

The fluid coupling 100 may be regarded as a two-piece fluid coupling 100, which, if desired, may consist of exclusively its main body with the first and optionally the second latching element 15, 17, as depicted in FIG. 1, as well as of the sealing element 200 of FIG. 2.

As seen in FIG. 3, but also already in FIG. 1, the tubular expansion of the second connecting section 5 may join or connect to the second end area 3 of the main body. It may, as depicted in FIG. 3, serve for receiving the sealing element 200 in its interior and hereunto be still radially wider as compared to the inner diameter of the second end area 3, i.e. having a larger diameter. The larger diameter allows the sealing element 200 to be arranged in the tubular expansion and concurrently in contact to the second end area 3, such that a passage from the second end area 3 to the sealing element 200 may be provided without a step or change of diameter.

In the depicted embodiment, the tubular expansion 5 has more than one diameter, each of which is larger than the inner diameter of the second end area 3 or of the fluid guiding section 1. In the example of FIG. 1 and FIG. 3, there are specifically at least two such diameters at which the sealing element 200 contacts each one peripheral section of the tubular expansion 5 respectively.

It is seen that the sealing element 200 is designed to contact both the front side of the mouth section of the fluid conduit 301 and a circumferential side (along the closed circumference) of the fluid conduit 301 at the fluid conduit 301. In this manner, a double sealing is established, one time at the front side, another time at the circumference, of the fluid conduit 301 respectively, i.e. both axially and radially. Such double sealing is possible by a stepped construction or design of the sealing element 200 which is established or achieved by providing more than only one inner diameter of the sealing element 200.

Figure 15:
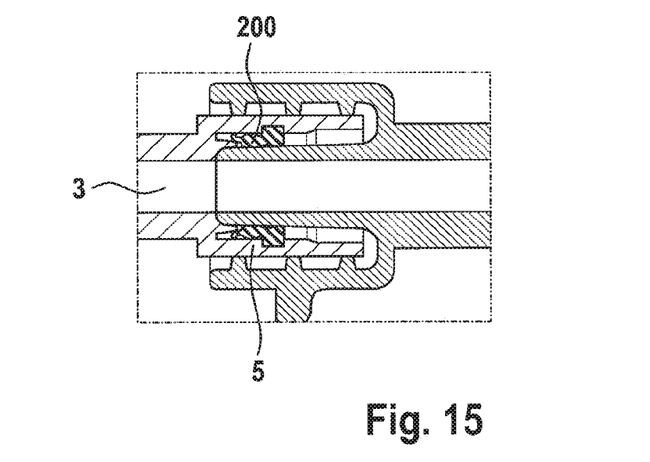
FIG. 15 shows a sealing element, alternative to that of FIG. 2, and its arrangement in a main body of the fluid coupling, alternative to that of FIG. 3.

It should be noted that the special design of the main body and/or of the tubular expansion 5 of the main body is adapted to the special design of the sealing element 200, as described herein. However, should a sealing element be provided, which does not prevent but allows, during use, a contact between second end area 3 and front side of the fluid conduit 301 of the connection section 300 (e.g., as shown in FIG. 15), then it is likewise encompassed in some embodiments.

Figure 4:
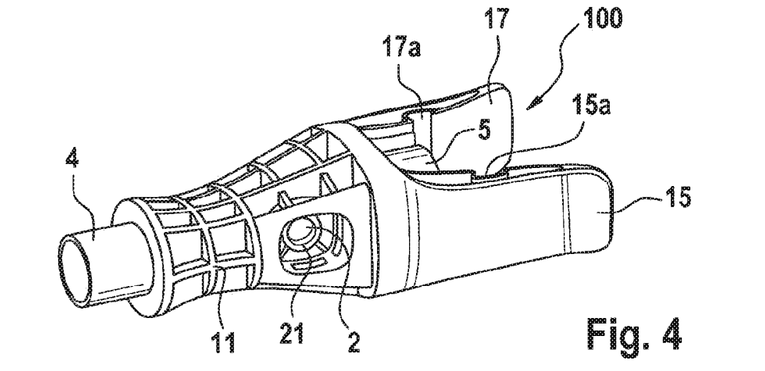
FIG. 4 shows a perspective view of a main body of a fluid coupling in a second embodiment with an additional opening as a further fluid connection to a fluid guiding section of the main body.

FIG. 4 shows a perspective view of a main body of an exemplary fluid coupling 100 in a second embodiment.

The fluid coupling 100 of this embodiment comprises the main body shown in FIG. 4, which differs from the main body of the fluid coupling 100 of FIG. 1 by having an addition or withdrawal opening 21. The opening 21 represents a portal facilitating fluid communication between an exterior of the fluid coupling 100 and the interior of the fluid guiding section 1 of the main body. The opening 21 is configured to allow the addition of fluid to the fluid flowing through the fluid coupling 100 in the fluid guiding section 1 between first end area 2 and second end area 3. The fluid added via the opening 21 may be medicament.

The opening 21 to the fluid guiding section 1 may be designed to be accessible from one side of the main body, e.g. a side of a grip section. The opening 21 serves for the adding, for example, of medicament to the fluid flowing through the fluid coupling 100 in the fluid guiding section 1 between first end area 2 and second end area 3.

The opening 21 is recognizably disposed in a recess of the main body. The opening 21 is closed, during use, by means of a septum 23, initially seen in FIG. 7 and exemplarily made of rubber. The recess establishes a space between the opening 21 or an outer surface of the rubber of the septum 23 on the one side, and an outer of the surface of the main body, e.g. the bar-honeycomb structure 11 on the other side. Such space ensures that the septum 23 cannot be touched by an operator because the opening 21 is too small for the finger to reach into it. The septum 23 is however at the same time accessible enough to be reached via a cannula or spray disinfection.

Figure 5:
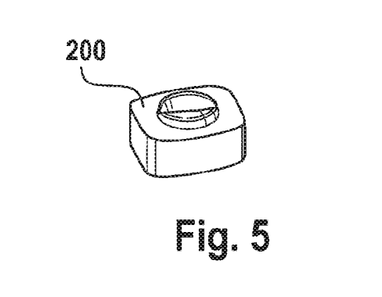
FIG. 5 shows a perspective view of a sealing element for use with the main body of FIG. 4.

FIG. 5 shows a sealing element 202 for the fluid coupling 100 of FIG. 4. It may optionally be used as the septum 23.

Figure 6:
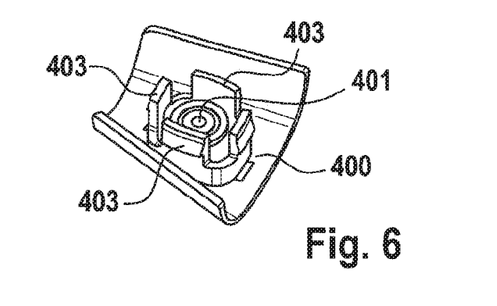
FIG. 6 shows a perspective view of a septum hood for use with the main body of FIG. 4.

FIG. 6 shows a septum hood 400 which may optionally be used together with the fluid coupling 100 of FIG. 4. The septum hood 400 may comprise a cover 401 whose back side is seen in FIG. 6 in the center of the septum hood 400. The cover 401 is closed in FIG. 9.

The septum hood 400 is designed to cover the recess, which is disposed in front of the opening 21 or the septum 23 with regard to the view of the user, against the main body of the fluid coupling 100.

The septum 23 may be repositioned by about 1 to 15 mm, preferably by about 2 to 10 mm, more preferably by about 3 to 5 mm.

The septum hood 400 may be designed with respect to the surface of the main body with which the septum hood 400 is flush to form a non-stepped closure of the recess.

The septum hood 400 may comprise hooks, detent lugs 403 or protrusions for fastening it to the main body. The main body may comprise corresponding recesses or undercuts for receiving or latching the septum hood 400. Other fastening modes are likewise envisioned within the scope of this disclosure.

Figure 7:
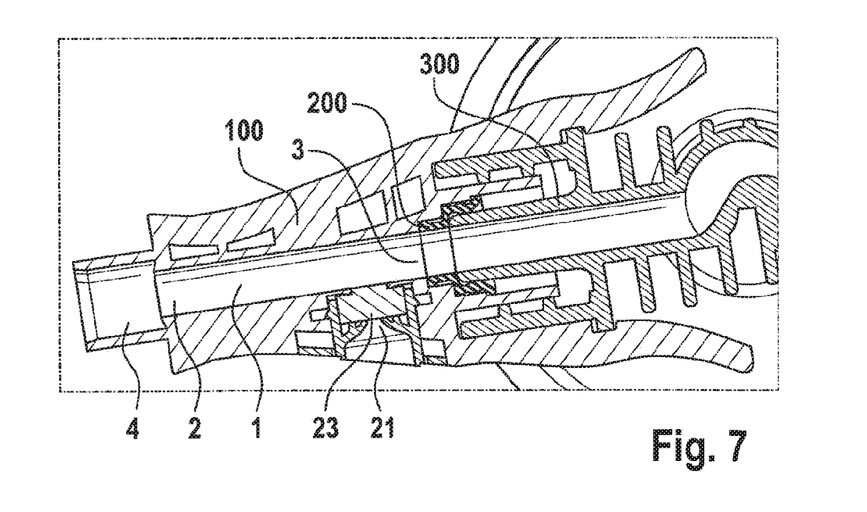
FIG. 7 shows a longitudinal section view of the fluid coupling of the second embodiment with the main body of FIG. 4, the sealing element of FIG. 5, and the septum hood of FIG. 6, wherein the fluid coupling is connected to a connection section.

FIG. 7 shows, in a longitudinal section, the fluid coupling 100 of FIG. 4 with a sealing element 200 of FIG. 2. Both are connected to the connection section 300 as intended. FIG. 7 shows thereby the system in a further exemplary embodiment.

The double, i.e. both radial and axial, fluidic sealing of the fluid guiding section 1 against the fluid conduit 301 of the connection section 300 by the sealing element 200 is also seen in the second embodiment of FIG. 7. Nevertheless, this feature is optional in each embodiment.

Figure 8:
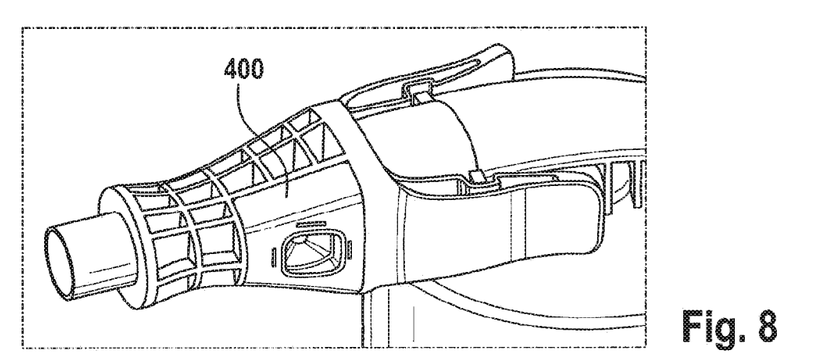
FIG. 8 shows the fluid coupling of FIG. 7 with septum hood, but with no cover, perspectively.

FIG. 8 shows the fluid coupling 100 of FIG. 4 with septum hood 400, however without cover 401.

Figure 9:
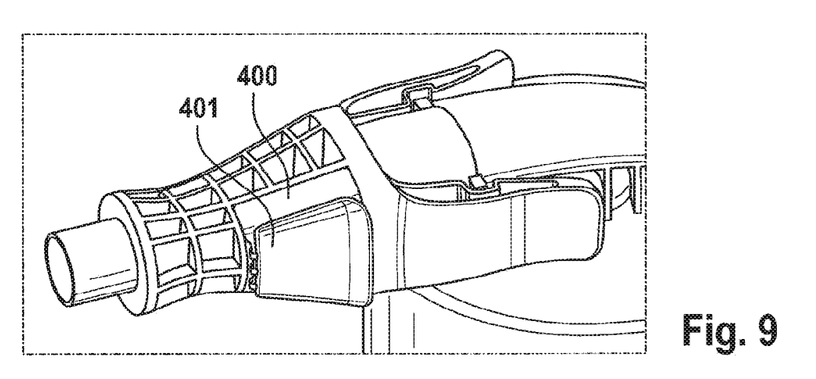
FIG. 9 shows the fluid coupling of FIG. 8 with closed cover of the septum hood, which is similar to that of FIG. 6.

FIG. 9 shows the fluid coupling 100 of FIG. 8 with closed cover 401 of the septum hood 400, which is again similar to that of FIG. 6.

Figure 10:
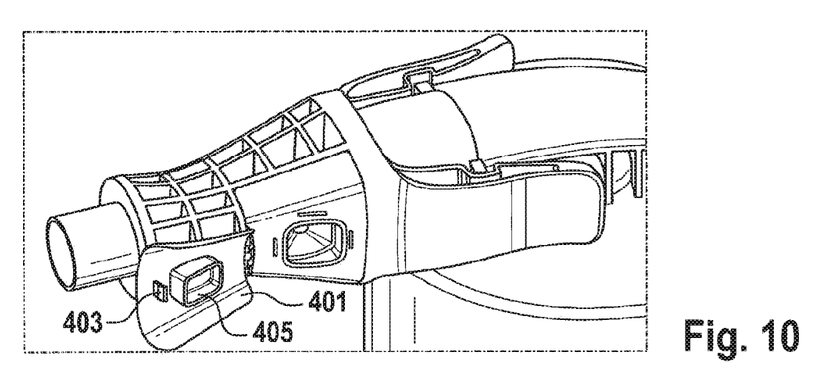
FIG. 10 shows the fluid coupling of FIG. 9 with septum hood having an opened cover.

FIG. 10 shows the fluid coupling 100 of FIG. 9 with septum hood 400 having an opened cover 401. A detent lug 403 and a sealing frame 405 are projecting from the cover 401, which has a circumferential edge that serves to fix the cover 401 geometrically to the septum hood 400. Furthermore, it may assist to seal the recess against fluid entry.

Figure 11:
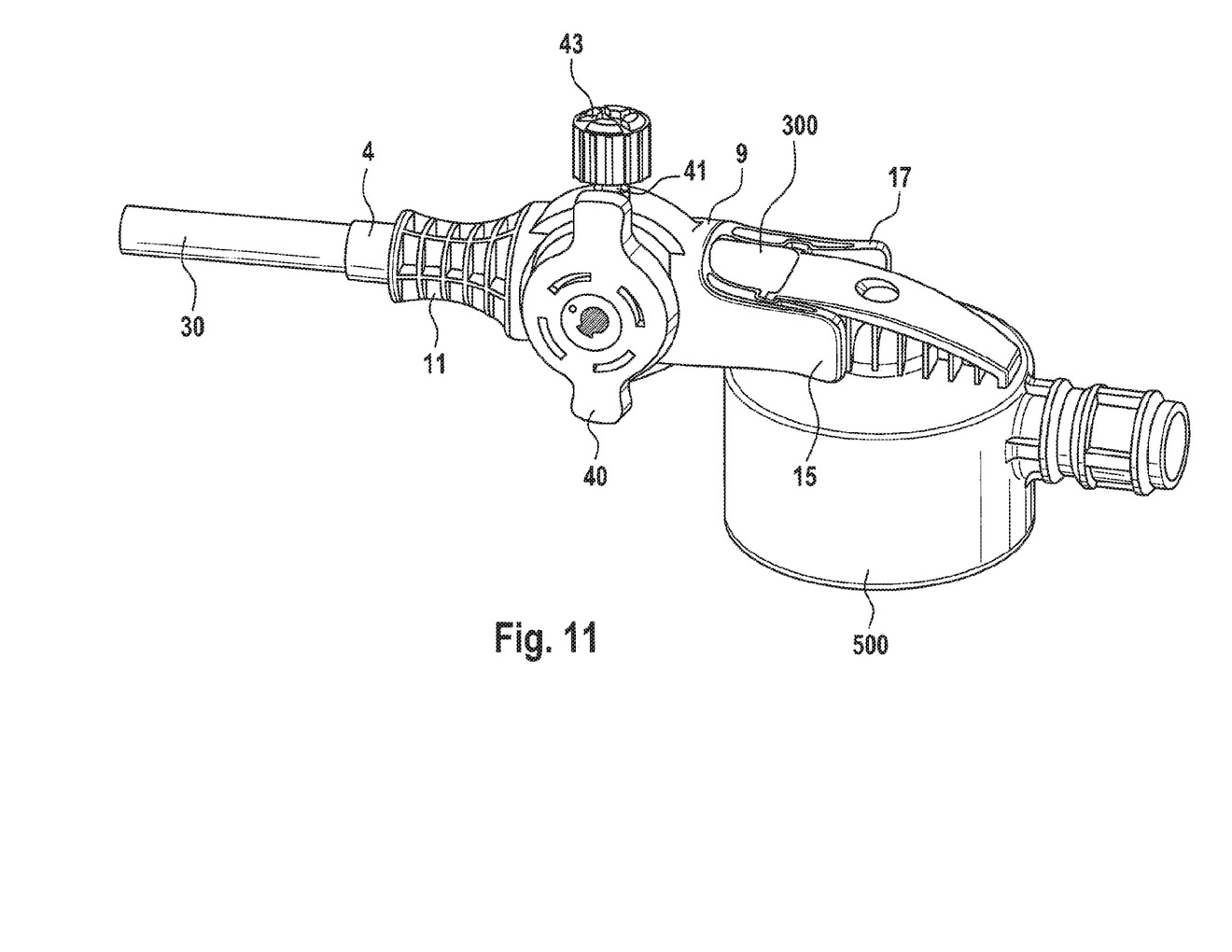
FIG. 11 shows a perspective view of the fluid coupling in a third embodiment connected to a blood treatment apparatus.

FIG. 11 shows a perspective view of the fluid coupling 100 in a third exemplary embodiment.

The fluid coupling 100 embodiment shown here includes an actuating element 40, for actuating or operating a multiway valve provided in the fluid coupling 100, as a further feature to the features which the fluid coupling 100 of the aforementioned first or second embodiment already comprise. The multiway valve serves for operating at least one secondary channel, which is contained in a secondary channel pipe 41. An optional protection cap has the reference numeral 43.

Further, the fluid coupling 100 is connected to the tube 30 or to the end of a tube line by the first connecting area 4. The connection section 300 is similarly in fluid communication with a blood treatment apparatus 500. Instead of being connected to the blood treatment apparatus 500 shown in FIG. 11, the connection section 300 may be in fluid communication with an adapter or may be part thereof.

FIG. 11 shows the fluid coupling 100 with a valve element, which is described in DE 10 2011 108 787 A1 as a port, operable by an actuating element 40. The relevant disclosure of which is hereby fully incorporated by reference.

Figure 12A:
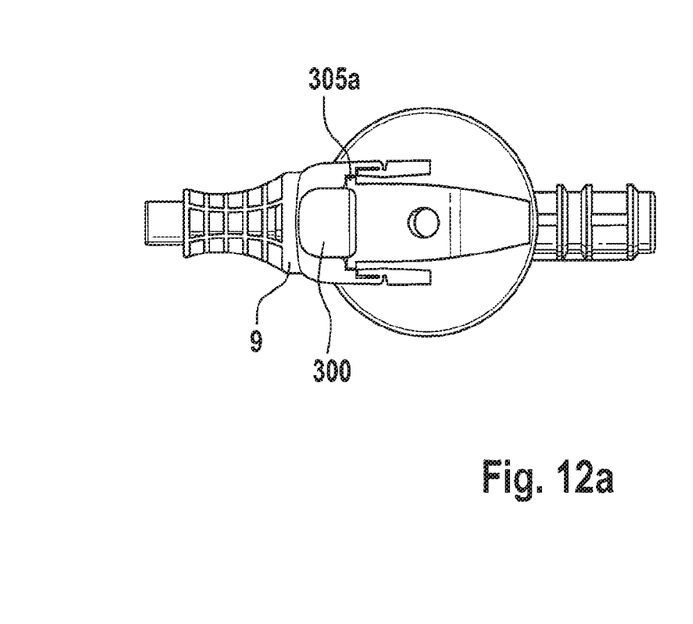
FIG. 12a, b show a top view, and two different positions, of the main body of a fluid coupling in a fourth embodiment as part of a system.
Figure 12B:
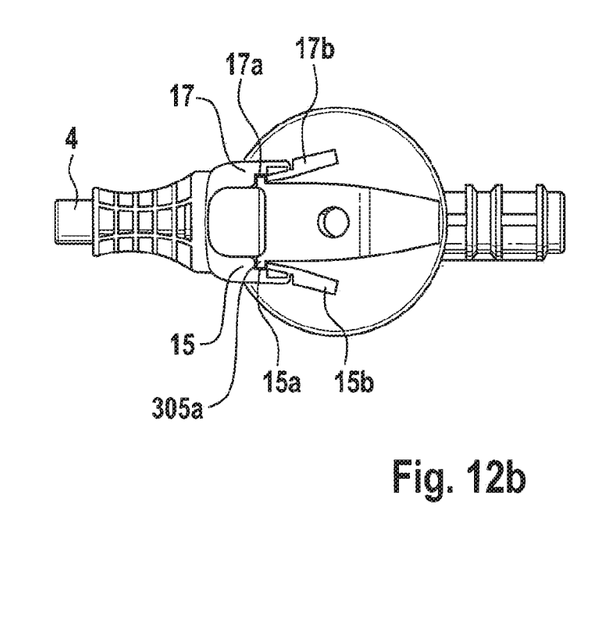

FIG. 12a, 12b show a top view of the main body of a fluid coupling 100 in a fourth embodiment and in two positions, one of which is shown in FIG. 12a and the other in FIG. 12b.

The connection process in the position shown in FIG. 12a, by which the fluid coupling 100 is shifted from left to right onto the connection section 300, is not yet complete, unlike in FIG. 12b. The position shown in FIG. 12a thus shows the fluid coupling 100 of this exemplary embodiment before the end of the connection process, which corresponds at the same time however also to the beginning of the release process, i.e. the process by which the fluid coupling 100 is released from the connection section 300.

The main body shown in FIG. 12a, b differs, with respect to its latching element 15, 17, from the main body of each of the aforementioned embodiments in that in the latter, the first elastic section 15b and the second elastic section 17b are each designed as, or comprise, a tiltable section having a front end and a back end, respectively. The front end is thereby closer to the first connecting section 4 than the back end. The latter may, as exemplarily shown in FIG. 12a, b, close the main body at or towards a side thereof. The tiltable section 15b, 17b is arranged, relative to the remaining latching element 15, 17 or main body respectively, to be tiltable or foldable against material restoring forces or material resistance.

By comparing FIG. 12a with FIG. 12b, it is recognizable that the main body shown herein in the fourth embodiment differs from those of the aforementioned figures in that the recesses 15a, 17a of the latching element 15, 17 come to exist only when no external forces are applied on the tiltable section 15b, 17b as first or second section. Such external forces include existing forces with which the user moves the back ends of both tiltable sections 15b, 17b towards each other, and forces with which the protrusions 305a push apart the front ends of both tiltable sections 15b, 17b.

Figure 13A:
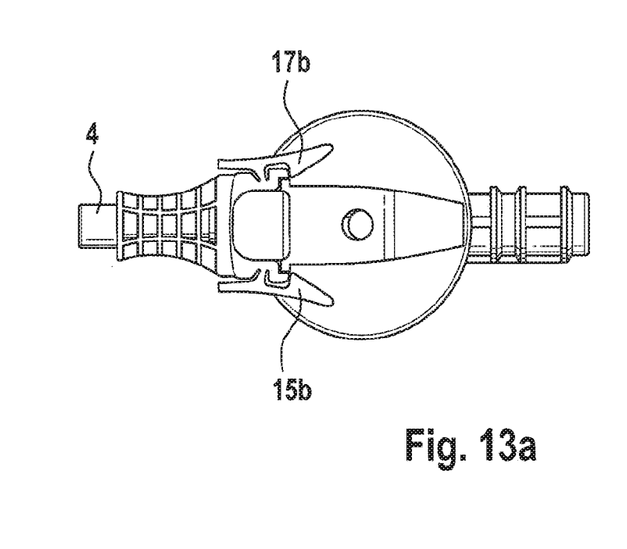
FIG. 13a, b show a top view of, and two different positions, the main body of a fluid coupling in a fifth embodiment as part of a system.
Figure 13B:
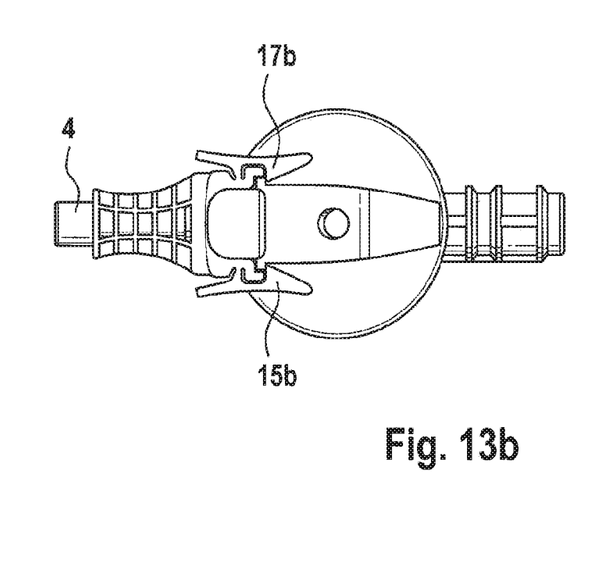

FIG. 13a, FIG. 13b show a top view of the main body of a fluid coupling 100 in a fifth embodiment and in two different positions, one of which is shown in FIG. 13a and the other in FIG. 13b.

In the position shown in FIG. 13a, the connection process, by which the fluid coupling 100 is shifted from left to right onto the connection section 300, is not yet completed, unlike in FIG. 13b. The position shown in FIG. 13a thus shows the fluid coupling 100 of this exemplary embodiment before the end of the connection process, which at the same time however also corresponds to the beginning of the release process, i.e. the process by which the fluid coupling 100 is to be released from the connection section 300.

The main body shown in FIG. 13a, b differs with respect to its latching element 15, 17 from the main body of FIG. 12a, b in that, the tiltable sections 15b, 17b may be opened when the user applies force onto the front end, such that the protrusion 305a is released, wherein the protrusion 305a pushes apart the back ends during the connection process.

In the designs of FIG. 12a, b and of FIG. 13a, b, unlike in the embodiments of FIGS. 1 to 10, there is thus no pressure applied to one and the same section of the latching element 15, 17 when connecting as well as when releasing of connection between recess 15a, 17a and protrusion 305a. In fact, by providing a tiltable section 15b, 17b, force is applied on a first end for connecting, and/or for release of the connection, force is applied on the opposite end of the tiltable section 15b, 17b. That advantageously allows offering a main body in which, depending on preferences of the user and with regard to the ergonomic and relevant mounting conditions, a spreading-apart, a moving apart, or a pressing together, a moving together may be required for releasing the connection.

The first and the second section 15b, 17b of the latching elements 15, 17 are designed as tiltable sections in the embodiments of FIG. 12a, b and of FIG. 13a, b.

Figure 14:
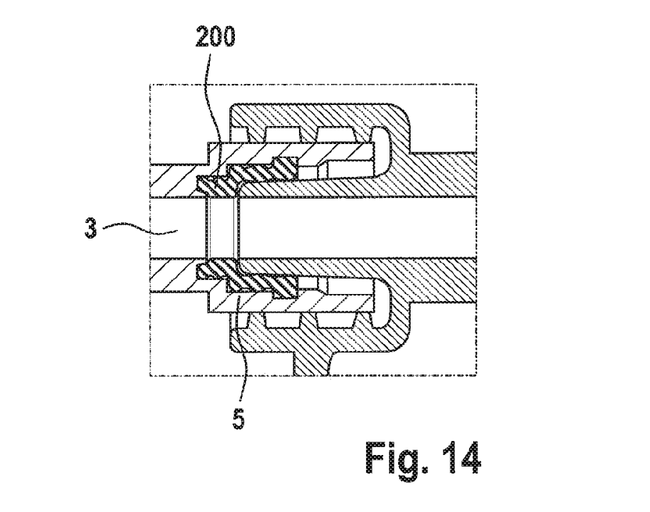
FIG. 14 shows the sealing element of FIG. 2 and its arrangement in the main body according to FIG. 3.

FIG. 14 shows the sealing element 200 of FIG. 2 and its arrangement in the main body according to FIG. 3, in which it prevents a direct contact between the end area 3 and the outlet of the fluid conduit 301.

FIG. 15 shows an alternative sealing element 200 and its arrangement in an alternative main body of the fluid coupling 100, in which it does not prevent a direct contact between the end area 3 and the outlet of the fluid conduit 301. It is rather arranged to abut an outer circumference of the fluid conduit 301 and an inner circumference of the tubular expansion 5, but not to abut a surface of the fluid conduit 301.

LIST OF REFERENCE NUMERALS 100 fluid coupling
1 fluid guiding section
2 first end area
3 second end area
4 first connecting section
5 second connecting section; tubular expansion
11 web-honeycombs structure
15 first latching or fixing element
15a recess
15b first section, tiltable section
15c free space or vacuity
17 second latching element
17a recess
17b second section, tiltable section
17c free space
19 third area
21 addition or withdrawal opening, shortly: opening
23 septum
25 peripheral groove
30 tube or tube line
40 actuating element
41 secondary canal or branching pipe
43 protection cap
200 sealing element
202 sealing element
210 peripheral bead
300 connection section
305a protrusions
301 fluid conduit
310 outer pipe
400 septum hood
401 cover
403 detent lug
405 sealing edge
500 blood treatment apparatus

The invention claimed is:

1. A medical fluid coupling configured to be connected to a connection section of a blood treatment apparatus or of a connecting adapter, the fluid coupling comprising:
   a sealing element comprising a first section, a second section, and a through opening through the first section and the second section; and
   a main body comprising:
      a receiving section configured for connecting to a fluid conduit of the connection section;
      a connecting section configured for connecting the fluid coupling to a fluid system; and
      a first latching element having a first section that is elastically bendable or elastically tiltable, the first latching element comprising at least one of: (i) a recess for receiving a protrusion of the connection section or (ii) a protrusion to reach into a recess of the blood treatment apparatus or of the connecting adapter, wherein:
         the at least one of the recess or the protrusion either faces the receiving section, or is arranged at an inner side of the first latching element, or both;
         the main body is made of or comprises a first material;
         the sealing element is made of a second material that is different from the first material;
         the main body defines a fluid guiding section therethrough for guiding a fluid through the fluid coupling in a longitudinal direction;
         a first inner diameter of the through opening through the first section of the sealing element is smaller than a second inner diameter of the through opening through the second section of the sealing element; and
         the first inner diameter of the through opening through the first section of the sealing element is equal to an inner diameter of the fluid guiding section, wherein the inner diameter of the fluid guiding section remains constant along a length of the fluid guiding section extending between a first end area of the fluid guiding section proximate the connecting section and a second end area of the fluid guiding section proximate the sealing element.

2. The fluid coupling of claim 1, wherein the main body further comprises a second latching element having a second section that is elastically bendable or elastically tiltable.

3. The fluid coupling of claim 2, wherein the first section of the first latching element and the second section of the second latching element are, in a non-connected state, arranged having a first distance between each other, and wherein, during a process of connecting the fluid coupling to the connection section, the first distance becomes a second distance which is larger than the first distance.

4. The fluid coupling of claim 2, wherein at least one of the first section of the first latching element and the second section of the second latching element is designed as a tiltable section or is arranged at a further section of the first and second latching elements in a tiltable manner.

5. The fluid coupling of claim 1, wherein the inner diameter of the fluid guiding section is between 4.0 and 4.5 mm.

6. The fluid coupling of claim 1, wherein the fluid guiding section therethrough comprises at least one further opening which is closed by a septum.

7. The fluid coupling of claim 1, wherein the fluid guiding section defines a main canal with a lumen for guiding a first fluid through the fluid coupling and defines a secondary canal with a secondary canal outlet for adding a second fluid into the main canal,
   wherein the fluid coupling comprises an actuating element arranged relative to the main body to be movable between a first position and a second position, and
   wherein the fluid coupling comprises a multiway valve which is operable, by movements of the actuating element, between: (i) a first position of the multiway valve in which the multiway valve does not close or cover the secondary canal outlet and (ii) a second position of the multiway valve in which the multiway valve closes or covers the secondary canal outlet.

8. The fluid coupling of claim 1, wherein the connecting section of the main body is configured to be connected to a tube line of the fluid system.

9. A system, comprising:
a fluid coupling; and
a connection section of a blood treatment apparatus or of a connecting adapter, wherein the fluid coupling comprises:
- a sealing element comprising a first section, a second section, and a through opening through the first section and the second section; and
- a main body comprising:
  - a receiving section configured for connecting to a fluid conduit of the connection section;
  - a connecting section configured for connecting the fluid coupling to a fluid system; and
  - a first latching element having a first section that is elastically bendable or elastically tiltable, the first latching element comprising at least one of: (i) a recess for receiving a protrusion of the connection section or (ii) a protrusion to reach into a recess of the blood treatment apparatus or of the connecting adapter, wherein;
    - the recess or the protrusion either faces the receiving section, or is arranged at an inner side of the first latching element, or both;
    - wherein the fluid coupling and the connection section are designed and provided to be latched together in a latching connection:
    - the main body is made of or comprises a first material;
    - the sealing element is made of a second material that is different from the first material;
    - the main body defines a fluid guiding section therethrough for guiding a fluid through the fluid coupling in a longitudinal direction;
    - a first inner diameter of the through opening through the first section of the sealing element is smaller than a second inner diameter of the through opening through the second section of the sealing element; and
    - the first inner diameter of the through opening through the first section of the sealing element is equal to an inner diameter of the fluid guiding section, wherein the inner diameter of the fluid guiding section remains constant along a length of the fluid guiding section extending between a first end area of the fluid guiding section proximate the connecting section and a second end area of the fluid guiding section proximate the sealing element.

10. The system of claim 9, wherein the inner diameter of the fluid guiding section and an inner diameter of the fluid conduit of the connection section are the same in an area of a front face assigned to or facing the fluid guiding section.

11. The system of claim 9, wherein the inner diameter of the fluid guiding section, the first inner diameter of the through opening through the first section of the sealing element, and an inner diameter of the fluid conduit are the same in an area of a front face assigned to or facing the fluid guiding section.

12. The system of claim 9, wherein the system comprises the connection section of the blood treatment apparatus.

13. The system of claim 9, further comprising a tube line connected to the fluid coupling.

14. The system of claim 13, wherein a length of the tube line is 100 mm maximally.

15. The system of claim 13, wherein the tube line is connected to the connecting section of the main body.

16. The system of claim 9, further comprising a blood treatment machine connected in fluid communication to the blood treatment apparatus or with the connecting adapter.

* * * * *